United States Patent [19]

Weigle et al.

[11] Patent Number: 4,683,221
[45] Date of Patent: Jul. 28, 1987

[54] LYMPHOCYTE-ACTIVATING POLYPEPTIDES

[75] Inventors: William O. Weigle, Del Mar; Monte O. Hobbs, Carlsbad; Edward L. Morgan; Marilyn L. Thoman, both of San Diego; Richard A. Houghten, Solana Beach, all of Calif.

[73] Assignee: Scripps Clinic and Research Foundation, La Jolla, Calif.

[21] Appl. No.: 817,526

[22] Filed: Jan. 9, 1986

[51] Int. Cl.$^4$ .................. A61K 37/02; C07K 5/10; C07K 7/06

[52] U.S. Cl. .................................. 514/14; 514/15; 514/16; 514/17; 514/18; 530/327; 530/328; 530/329; 530/330; 530/388

[58] Field of Search .............. 530/330, 227, 228, 229, 530/388; 514/14, 15, 16, 17, 18

[56] References Cited

U.S. PATENT DOCUMENTS 4,415,493 11/1983 Weigle et al. .................. 530/388

4,579,840 4/1986 Hahn .................. 530/329

OTHER PUBLICATIONS

Morgan et al., Proc. Natl. Acad. Sci. USA, vol. 79, pp. 5388–5391, Sep. 1982.

Reitcliffe et al., Biological Abstract, vol. 74, No. 83493, 1982.

*Primary Examiner*—Delbert R. Phillips
*Assistant Examiner*—Christina Chan
*Attorney, Agent, or Firm*—Dressler, Goldsmith, Shore, Sutker & Milnamow, Ltd.

[57] ABSTRACT

A lymphocyte-activating polypeptide, a composition containing the polypeptide and a method for using the composition are disclosed. The polypeptide contains a sequence of 4 to about 11 residues and corresponds in sequence to the formula:

$$(B)_b\text{-Leu-Pro-Pro-Ser-}(Y)_y.$$

15 Claims, 2 Drawing Figures

GENERATION OF BCDF FROM MOUSE SPLEEN CELLS
BY SYNTHETIC Fc PEPTIDES

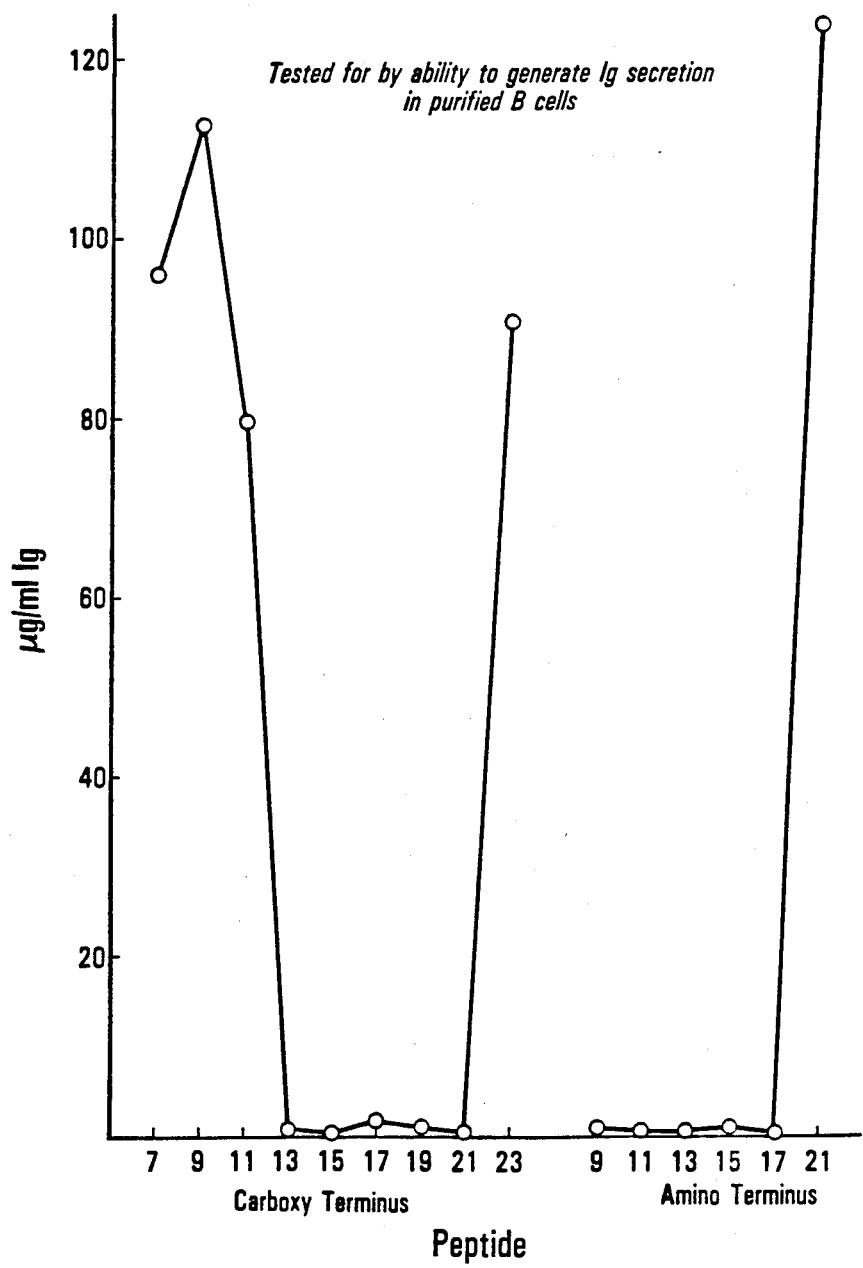

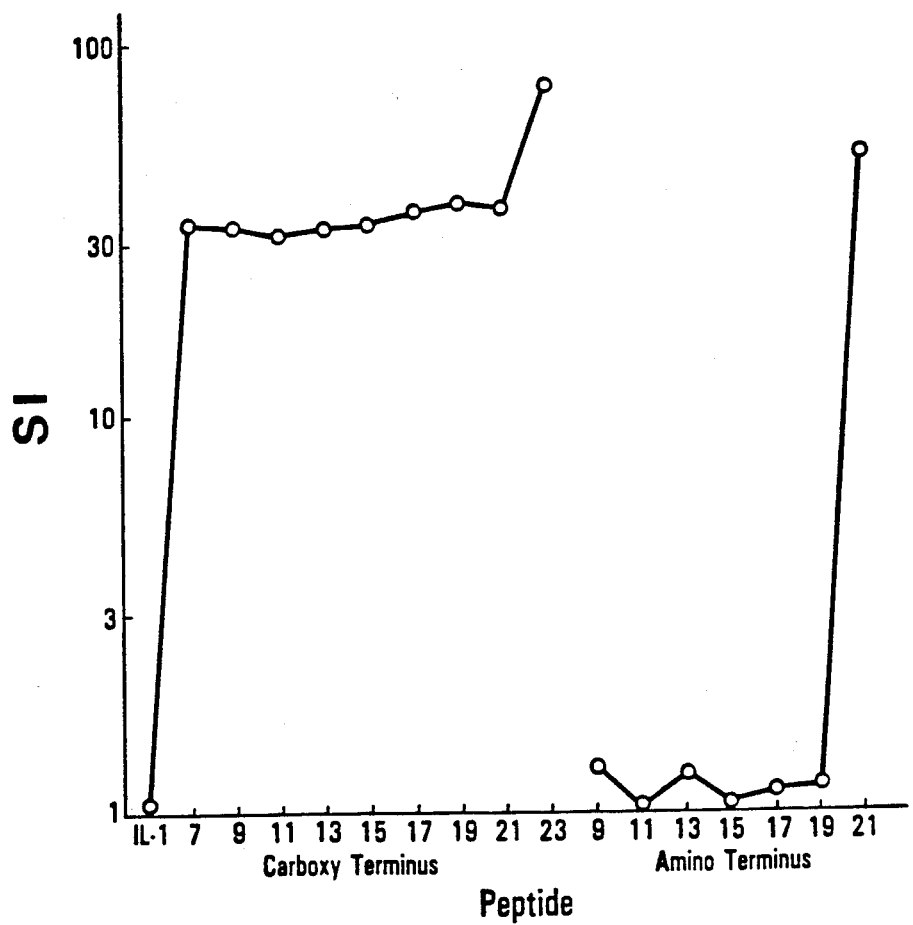

LYMPHOCYTE-ACTIVATING POLYPEPTIDES

DESCRIPTION

1. Technical Field

This invention is directed to polypeptides that are useful in activating mammalian lymphocytes, as well as compositions containing a lymphocyte-activating polypeptide and a method for using such a composition.

2. Background

Immunoglobulins are proteins produced by plasma cells as one of the later in a complex sequence of events initiated by antigen challenge of the host. The plasma cells, as another part of this sequence, are derived from B lymphocytes that have become activated by a mechanism or series of mechanisms that, to date, are not fully understood.

There are five classes of recognized immunoglobulins: IgG, IgA, IgM, IgD, and IgE. Of these, IgG represents the major portion of circulating immunoglobulins.

The immunoglobulin protein molecule, often referred to as an "Ig molecule", is composed of four interconnected polypeptide chains, two of which are termed "light" (L) chains and two "heavy" (H) chains. Under this arrangement, the Ig molecule is divided into two identical portions, each of which comprises a light and a heavy chain linked by disulfide bridges formed from cystine residues. The two resulting portions, in turn, are linked by disulfide bridges.

Each of the four chains is composed generally of two portions, a variable region ($V_L$ and $V_H$) extending from the amino-terminus and having highly variable amino acid residue sequences, and a constant region ($C_L$ and $C_H$) extending from the carboxy-terminus and having generally constant amino acid residue sequences. Each of these regions represents a discrete portion of the Ig molecule. The $C_H$ region is further subdivided into three domains designated $CH_1$, $CH_2$ and $CH_3$, on the basis of constant regions of homology.

It has been known for a number of years that the Ig molecule can be enzymatically cleaved into discrete fragments. The properties of these fragments then have been determined using a variety of biological assay systems.

Using papain, the IgG molecule can be cleaved, producing an "Fc" fragment and two "Fab" fragments. The Fc fragment represents the carboxy-terminal portions of the two heavy chains joined by a disulfide bridge, and each of the Fab fragments is composed of the amino-terminal portion of the heavy chain and the entire light chain joined by disulfide bridges.

Pepsin and plasmin cleavages of the IgG molecule occur at sites closer to the heavy chain carboxy-terminus and downstream of the disulfide bridge that joins the two heavy chains. The pepsin product, termed the "pFc'" fragment, and the plasmin product, represent carboxy-terminal portions of the Fc fragment ($CH_3$ domain of IgG).

It has been recognized that certain biological activities reside in the Fc and pFc' fragments. Thus, mouse spleen B lymphocytes are induced to proliferate in the presence of papain-derived Fc fragments, [M. A. Berman and W. O. WEIGLE, J. Exp. Med., 146, 241 (1977)]. Furthermore, it has been observed that the proliferative response is dependent upon the presence of macrophages. It appears that macrophages enzymatically cleave the Fc fragment to a 14,000 MW subfragment, and the latter stimulates B cell proliferation [E. L. Morgan and W. O. Weigle, J. Exp. Med., 150, 256 (1979); and E. L. Morgan and W. O. Weigle, J. Exp. Med., 151, 1 (1979)].

Subsequently, it was shown that the Fc fragment has the ability in the presence of both macrophages and T cells to induce a polyclonal antibody response in mouse spleen cells [E. L. Morgan and W. O. Weigle, J. Immun., 124, 1330 (1980)]. It was also shown that the shorter fragment produced by plasmin digestion of IgG is active in producing a polyclonal antibody response [E. L. Morgan and W. O. Weigle, J. Supra-molecular Structure, 14, 201 (1980)].

The polypeptides described in co-assigned U.S. Pat. No. 4,415,493, whose disclosures are incorporated herein by reference, are useful in modulating the immune response and are available either synthetically using readily available polypeptide synthesis methods or by enzymatic and chemical cleavage of the IgG molecule. When produced by cleavage methodology, the IgG first is digested with plasmin after which the resulting segments are treated with cyanogen bromide.

The resulting active fragment comprises 23 amino acid residues defined by residues of sequence positions 335-357 of the IgG molecule of which it was a part. The carboxy-terminal residue of the 24-residue polypeptide that is actually produced is homoserine (Hse), and results from the methionine that was at residue position 358, the site of the CNBr cleavage.

For an illustration of these sequences, see, for example, the sequence described in G. M. Edelman et al., Proc. Natl. Acad. Sci, USA, 663, 78 (1969). A further discussion of the 23- and 24-residue polypeptides and their immune response-modulating capacities can be found in Morgan et al., J. Exp. Med., 157, 947-956 (1983) and in Morgan et al., Pro. Natl. Acad. Sci., USA, 79, 5388-5391 (1982), both of whose disclosures are also incorporated by reference.

BRIEF SUMMARY OF THE INVENTION

A new class of even shorter lymphocyte-activating polypeptides now has been discovered. These polypeptides, defined by this invention, exhibit lymphocyte activation in terms of their ability to cause polyclonal Ig molecule secretion, proliferation of lymphocytes and induction of lymphocytes to release B cell differentiation factor (BCDF).

The present invention contemplates these polypeptides, a composition that contains an effective amount of such a polypeptide, and a method of activating lymphocytes by contacting those cells with a unit dose of a composition that contains a polypeptide of this invention.

A polypeptide of this invention contains 4 to about 11 residues and has an amino acid residue sequence, written from left to right and in the direction from amino-terminus to carboxy-terminus, that corresponds to the formula:

$(B)_b$-Leu-Pro-Pro-Ser-$(Y)_y$ and the pharmaceutically acceptable non-toxic salts thereof, wherein B is the amino acid residue Thr or is a peptide, written from left to right and in the direction from amino-terminus to carboxy-terminus, selected from the group consisting of Tyr-Thr, Val-Tyr-Thr, and Gln-Val-Tyr-Thr;

Y is the amino acid residue Arg, or is a peptide, written from left to right and in the direction from amino-terminus to carboxy-terminus, selected from the group consisting of Arg-Glu and Arg-Glu-Glu; and b and y are each independently one or zero, such that when either or both of b and y are zero, the respective B and Y are absent, and when either or both of b and y are one, the respective B and Y are present.

A composition of this invention comprises an effective amount of a before-described polypeptide as the active ingredient admixed with a physiologically tolerable diluent. Mammalian lymphocytes are activated by contacting such lymphocytes with one or more unit doses of a composition of this invention. Such contactng can be effected in vitro or in vivo.

The present invention has several benefits and advantages.

A salient benefit of the invention is the ability of a relatively short polypeptide to activate lymphocytes where heretofore such activation was only possible with an Fc fragment or a polypeptide about two to four times the length used herein; i.e., about 23 amino acid residues long.

An advantage of the invention is that the lymphocyte activation obtained is substantially identical to that obtained with the above-mentioned 23-residue polypeptide.

Still further benefits and advantages of the invention will be apparent to those skilled in the art from the detailed description that follows.

BRIEF DESCRIPTION OF THE DRAWINGS

In the drawings forming a portion of this disclosure,

FIG. 1 is a graph showing the generation of B cell differentiation factor (BCDF) from mouse spleen cells by contacting those cells with various compositions, including compositions of this invention. The spleen cell supernatants were then contacted with a suspension of lymphocytes depleted of T cells and macrophages to induce the production of Ig molecules that were measured in micrograms per milliliter (ug/ml Ig; ordinate). The abscissa is shown in terms of polypeptides (Peptide) of 7, 9, 11, 13, 15, 17, 19, 21 and 23 residues from the carboxy-terminus and 9, 11, 13, 15, 17 and 21 residues from the amino-terminus of the 23 residue polypeptide of U.S. Pat. No. 4,415,493 that corresponds to the residues 335-357 of the human IgG1 molecule of a human myeloma protein and are located in the Fc CH$_3$ domain, using procedures described hereinafter; and FIG. 2 is a graph showing the proliferation of mouse B cells as measured by the uptake of radio-labeled thymidine and expressed as a Stimulation Index (SI) that is determined as the ratio of the counts per minute (cpm) of an assayed sample to the background cpm (ordinate), and caused by contacting those cells with a composition containing interleukin-1 (IL-1) alone or in combination with a polypeptide of FIG. 1 (Peptide), using procedures described hereinafter.

DETAILED DESCRIPTION OF THE INVENTION

The present invention contemplates a lymphocyte-activating polypeptide, a composition containing an effective amount of such a polypeptide as an active lymphocyte-activating ingredient, and a method of activating lymphocytes using a unit dose of such a composition to contact the lymphocytes.

The polypeptides of this invention correspond in sequence to a portion of human IgG1 myeloma protein in the CH$_3$ domain of the Fc portion. However, as discussed hereinafter, these polypeptides have activities that are both similar and different from those of the 14,000 dalton myeloma protein Fc portion, and the 23- and 24-residue polypeptides disclosed in U.S. Pat. No. 4,415,493, that correspond to position 335-357 and 335-358 of that IgG1 molecule.

A. Polypeptides

A polypeptide of this invention contains a sequence of 4 to about 11 amino acid residues, written from left to right and in the direction from amino-terminus to carboxy-terminus, corresponds to the formula:

(B)$_b$-Leu-Pro-Pro-Ser-(Y)$_y$ and the pharmaceutically acceptable non-toxic salts thereof, wherein B is the amino acid residue Thr or is a peptide, written from left to right and in the direction from amino-terminus to carboxy-terminus, selected from the group consisting of Tyr-Thr, Val-Tyr-Thr, and Gln-Val-Tyr-Thr;

Y is the amino acid residue Arg, or is a peptide, written from left to right and in the direction from amino-terminus to carboxy-terminus, selected from Arg-Glu and Arg-Glu-Glu; and b and y are each independently one or zero, such that when either or both of b and y are zero, the respective B and Y are absent, and when either or both of b and y are one, the respective B and Y are present.

A polypeptide of this invention contains at least the amino acid residue sequence, written from left to right and in the direction from amino-terminus to carboxy-terminus, that corresponds to the formula:

Leu-Pro-Pro-Ser.

The above four-residue amino acid sequence corresponds to positions 351 through 354 of the human IgG1 myeloma protein.

Additionally useful polypeptides include the tetramer shown above and can additionally include a sequence of one to three amino acid residues at the carboxy-terminus, a sequence of one to four amino acid residues at the amino-terminus, or a sequence of one to three amino acid residues at the carboxy-terminus and a sequence of one to four amino acid residues at the amino-terminus. The amino acid residues at the carboxy-terminus correspond in sequence to the residues of positions 355 though 357 of the human IgG1 myeloma protein, while the residues at the amino-terminus correspond in sequence to positions 350 through 347 of that protein. These additional residues are encompassed by the before-defined formula:

(B)$_b$-Leu-Pro-Pro-Ser(Y)$_y$.

Exemplary, useful polypeptides, written from left to right and in the direction from aminoterminus to carboxy-terminus, correspond to the formulas:

Gln-Val-Tyr-Thr-Leu-Pro-Pro-Ser-Arg-Glu-Glu;

Val-Tyr-Thr-Leu-Pro-Pro-Ser-Arg-Glu-Glu;

Tyr-Thr-Leu-Pro-Pro-Ser-Arg-Glu-Glu;

Thr-Leu-Pro-Pro-Ser-Arg-Glu-Glu;

Leu-Pro-Pro-Ser-Arg-Glu-Glu;

Leu-Pro-Pro-Ser-Arg-Glu;

Leu-Pro-Pro-Ser-Arg;

Thr-Leu-Pro-Pro-Ser-Arg-Glu;

Tyr-Thr-Leu-Pro-Pro-Ser-Arg-Glu;

Val-Tyr-Thr-Leu-Pro-Pro-Ser-Arg-Glu;

Gln-Val-Tyr-Thr-Leu-Pro-Pro-Ser-Arg-Glu;

and the like.

It is believed that polypeptides carboxy-terminated with an Arg residue are cleaved quickly in mammalian blood by the enzyme carboxy peptidase to a corresponding polypeptide that is carboxy-terminated with the Ser residue that is present in each sequence.

A polypeptide of this invention can be prepared by any of a number of well known methods. However, it is preferred to use the Merrifield solid-phase synthesis method as is described in U.S. Pat. No. 4,415,493, No. 4,544,500 and No. 4,545,931, whose disclosures are incorporated by reference.

The before-described polypeptides are useful herein as are the pharmaceutically acceptable non-toxic salts of such polypeptides.

The polypeptides contain a basic amino-terminal amine group and can also contain a more basic Arg residue, and as such can form acid addition salts. Pharmaceutically acceptable, non-toxic acid addition salts of a polypeptide can be formed by treatment of the polypeptide with an appropriate acid. Exemplary inorganic acids include hydrochloric, hydrobromic, sulfuric, phosphoric and the like acids. Exemplary organic acids include acetic, propionic, glycolic, pyruvic, malonic, succinic, maleic, fumaric, malic, tartaric, citric, benzoic, cinnamic, mendelic, methanesulfonic, ethanesulfonic, benzenesulfonic, p-toluenesulfonic, salicyclic, p-aminosalicylic and the like acids. Conversely, the acid addition salt form can be converted to the free base form by treatment with alkali.

A useful polypeptide also includes a carboxy-terminal carboxylic acid and also include carboxylic acids from Glu residues, as already noted. Basic salts of those carboxylic acids are also contemplated, and are formed by treatment of a polypeptide with an appropriate alkaline reagent to form a polypeptide carboxylate cation salt. Exemplary non-toxic cation salts of such polypeptide carboxylic acids include sodium, potassium, zinc, aluminum, calcium, magnesium, and the like.

More preferred polypeptides contain at least six amino acid residues, and include polypeptides, written as described before, that correspond to the formulas:

Leu-Pro-Pro-Ser-Arg-Glu; and

Tyr-Thr-Leu-Pro-Pro-Ser.

Particularly preferred polypeptides contain at least seven amino acid residues, and include the polypeptides, written as described before, that correspond to the formulas:

Leu-Pro-Pro-Ser-Arg-Glu-Glu;

Tyr-Thr-Leu-Pro-Pro-Ser-Arg-Glu-Glu; and

Gln-Val-Tyr-Thr-Leu-Pro-Pro-Ser-Arg-Glu-Glu.

B. Compositions and Contacting of Cells

The polypeptides of this invention and compositions containing an effective amount of polypeptide, in view of their effect in activating lymphocytes, have wide applicability. They can be used, for example, in immunodeficiencies; viral, parasitic, and certain bacertial infections; and a wide range of autoimmune diseases. The polypeptides can also be used as an adjuvant for immunization as a prophylactic measure.

The polypeptides of this invention can be used in a variety of pharmaceutical compositions and formulations and can be administered by a variety of conventional routes, including parenteral routes such as intramuscular, intravenous, subcutaneous, intraperitoneal, as well as being administered orally.

In administering the compounds of this invention parenterally, the pharmceutical forms suitable for injection include sterile, liquid, aqueous solutions or dispersions and sterile powders for reconstitution into sterile injectable solutions or dispersions. The carrier can be a solvent or dispersing medium containing, for example, water, ethanol, polyol (for example glycerol, propylene glycol, liquid polyethylene glycol, and the like), suitable mixtures thereof, and vegetable oils. Proper fluidity can be maintained, for example, by the use of a coating such as lecithin, by the maintenance of the required particle size in the case of dispersion and by the use of surfactants. Prevention of the action of microorganisms can be ensured by various antibacterial and antifungal agents, for example, parabens, chlorobutanol, phenol, sorbic acid, and the like. In many cases, it is desirable to incude isotonic agents, for example, sugars, sodium chloride, and the like. Prolonged absorption of the injectable pharmaceutical form can be brought about by the use of agents delaying absorption, for example, aluminum monostearate and gelatin.

Sterile injectable solutions can be prepared by incorporating a polypeptide of this invention in the required amount of the appropriate solvent with various of the other ingredients, as desired. If desired, and for more effective distribution, a polypeptide can be incorporated into slow release or targeted delivery systems such as polymer matrices, liposomes, and microspheres.

As noted, a polypeptide of this invention can also be administered orally. It can be used with an inert diluent or a pharmaceutical carrier that can take the form of capsules, tablets, suspensions, emulsions, solutions, dispersible powders, and the like. A polypeptide of this invention can be administered either alone or as a mixture of a plurality of active ingredients in which the polypeptide is the lymphocyte-activating active ingredient. Preferably, an effective amount of a polypeptide is admixed with a diluent amount of a physiologically carrier, as above described, when administered.

Doses of the compounds of this invention are administered to the recipient to contact lymphocytes for a period during which lymphocyte activation is desired. The weight of the recipient, the polypeptide length and mode of administration have an influence upon the size of the dose necessary to induce a particular response. Generally, for parenteral administration, the dose is from about 200 micrograms (ug) to about 20 milligrams (mg) per kilogram (kg) body weight of the recipient per day throughout the period of desired lymphocyte activation. Preferably, the polypeptide is administered in an amount from abut 500 ug to about 5 mg per kg body weight daily.

Concentrations for the in vitro contacting of lymphocytes are about $1 \times 10^{-7}$ molar to about $1 \times 10^{-3}$ molar for cell concentrations of about $1 \times 10^6$ cells per milliliter.

An active ingredient polypeptide of this invention is contacted with lymphocytes to be activated in vitro in cell culture or in vivo by oral or parenteral administration to a mammal in a customary unit dosage composition; i.e., as a composition in unit dosage form comprising a physiologically tolerable carrier admixed with an effective amount of a useful polypeptide.

The term "unit dosage" and its grammatical equivalents as used herein refer to physically discrete units suitable as unitary dosages for human patients and mammals, each unit containing a predetermined effective amount of the active ingredient calculated to produce the desired therapeutic effect in association with the required physiologically tolerable carrier, e.g. a diluent or a vehicle. The specifications for the novel unit dosage forms of this invention are dictated by and are directly dependent on (a) the unique characteristics of the active ingredient polypeptide and the particular therapeutic effect to be achieved, and (b) the limitations inherent in the art of compounding such an active ingredient for therapeutic use in vitro, as well as in vivo in humans and other mammals. Examples of suitable unit dosage forms in accord with this invention are liquid solutions, emulsions and suspensions, and segregated multiples of any of the foregoing, as already noted.

Contact between the composition and mammalian lymphocytes is maintained for a time period sufficient for the contacted lymphocytes to manifest activation. Lymphocyte activation can itself be manifest in cellular proliferation, enhanced antibody secretion, BCDF secretion, and the like.

For use in vivo, contact between mammalian cells and optimal concentrations of the composition is typically maintained for a time period sufficient for the animal to clear the polypeptide from its body as by metabolism, excretion or both processes. That time period can be longer than that required for lymphocyte activation to be manifest.

Contact in vitro can be maintained for a period of time sufficient for one of the before-described cellular functions to become manifest as determined by standard assay techniques. Such maintenance times typically take about one to about seven days of time, and more usually about 2 to about 5 days.

C. Lymphocyte Activation and Assays

The polypeptides of this invention activate lymphocytes when such cells are contacted with a composition of this invention that contains an effective amount of polypeptide. That activation occurs when the contacting is carried out in vitro and in vivo. The discussion that follows describes in vitro activation of T cells to produce B cell differentiation factor (BCDF), activation of B cells to exhibit on enhanced polyclonal antibody response, as well as activation of a mixed lymphocyte culture to proliferate.

1. Polyclonal Antibody Response and Assay

This assay measures the activity of a polypeptide in potentiating an in vitro polyclonal antibody response using mouse spleen cells.

For the generation of immunoglobulin (Ig) secretion response, spleen cells from inbred male 8-15 week old C57BL/6 mice (The Jackson Laboratory, Bar Harbor, ME) were suspended in RPMI 1640 medium (M.A. Bioproducts, Walkersville, MD) supplemented with 2 millimolar (mM) L-glutamine, one percent BME vitamins (GIBCO, Grand Island, NY), $5 \times 10^{-5}$ molar (M) 2-mercaptoethanol, 7.5 percent fetal calf serum (FCS;GIBCO), and 0.001 percent gentamicin (Schering Corp., Kenilworth, NJ). Cells ($6 \times 10^5$) in 0.2 milliliters (ml) of the supplemented medium were added to flat-bottomed microtiter plate wells (No. 3596: Costar, Cambridge, MA). Cultures were established in triplicate, and a polypeptide-containing composition was added in a volume of 50 microliters per well (ul/well).

To establish comparison between polypeptides of different lengths, equimolar amounts of polypeptide were used, with 1.5 milligrams per milliliter (mg/ml) of the 23-residue polypeptide corresponding in sequence to positions 335-357 of the human IgG1 myeloma protein as standard. (That 23-residue polypeptide is also referred to herein as polypeptide p23.) The plates were then maintained (incubated) for 5 days at 37° C. in an atmosphere containing 5 percent $CO_2$ in air before the response was assayed. Supernatants from triplicate cell culture wells were harvested, pooled, centrifuged to remove cells and stored at $-20°$ C. Concentrations of Ig in the supernatants were determined by the ELISA assay described hereinbelow.

Results of the polyclonal antibody response assay are shown in Table 1, below, and are expressed as total amount of Ig molecules in ug/ml that was found to be secreted into the supernatant as a result of those cells being contacted with a polypeptidecontaining composition. These results are also summarized in column 4 of Table 3 hereinafter.

TABLE 1

| Peptide[1] | POLYCLONAL Ig MONOCLONAL SECRETION INDUCED BY SYNTHETIC POLYPEPTIDES Polypeptide Sequence[1] | Ig Found[3] |
|---|---|---|
| (P23) | Thr-Ile-Ser-Lys-Ala-Lys-Gly-Gln-Pro-Arg-Glu-Pro-Gln-Val-Tyr-Thr-Leu-Pro-Pro-Ser-Arg-Glu-Glu | 12.7 |
| 1-52(a) | Thr-Ile-Ser-Lys-Ala-Lys-Gly-Gln-Pro | 1.5 |
| (b) | Thr-Ile-Ser-Lys-Ala-Lys-Gly-Gln-Pro-Arg-Glu | 2.2 |
| (c) | Thr-Ile-Ser-Lys-Ala-Lys-Gly-Gln-Pro-Arg-Glu-Pro-Gln | 1.9 |
| (d) | Thr-Ile-Ser-Lys-Ala-Lys-Gly-Gln-Pro-Arg-Glu-Pro-Gln-Val-Tyr | 1.8 |
| (e) | Thr-Ile-Ser-Lys-Ala-Lys-Gly-Gln-Pro-Arg-Glu-Pro-Gln-Val-Tyr-Thr-Leu | 1.9 |
| (f) | Thr-Ile-Ser-Lys-Ala-Lys-Gly-Gln-Pro-Arg-Glu-Pro-Gln-Val-Tyr-Thr-Leu-Pro-Pro | 1.5 |
| (g) | Thr-Ile-Ser-Lys-Ala-Lys-Gly-Gln-Pro-Arg-Glu-Pro-Gln-Val-Tyr-Thr-Leu-Pro-Pro-Ser-Arg | 11.7 |
| 1-51(a) | Leu-Pro-Pro-Ser-Arg-Glu-Glu | 10.2 |
| (b) | Tyr-Thr-Leu-Pro-Pro-Ser-Arg-Glu-Glu | 10.7 |
| (c) | Gln-Val-Tyr-Thr-Leu-Pro-Pro-Ser-Arg-Glu-Glu | 11.7 |
| (d) | Glu-Pro-Gln-Val-Tyr-Thr-Leu-Pro-Pro-Ser-Arg-Glu-Glu | 1.9 |

TABLE 1-continued
POLYCLONAL Ig MONOCLONAL SECRETION INDUCED BY SYNTHETIC POLYPEPTIDES

| Peptide[1] | Polypeptide Sequence[1] | Ig Found[3] |
|---|---|---|
| (e) | Pro-Arg-Glu-Pro-Gln-Val-Tyr-Thr-Leu-Pro-Pro-Ser-Arg-Glu-Glu | 1.3 |
| (f) | Gly-Gln-Pro-Arg-Glu-Pro-Gln-Val-Tyr-Thr-Leu-Pro-Pro-Ser-Arg-Glu-Glu | 1.7 |
| (g) | Ala-Lys-Gly-Gln-Pro-Arg-Glu-Pro-Gln-Val-Tyr-Thr-Leu-Pro-Pro-Ser-Arg-Glu-Glu | 1.5 |
| (h) | Ser-Lys-Ala-Lys-Gly-Gln-Pro-Arg-Glu-Pro-Gln-Val-Tyr-Thr-Leu-Pro-Pro-Ser-Arg-Glu-Glu | 1.3 |
| (i) | <u>Thr-Ile-Ser-Lys-Ala-Lys-Gly-Gln-Pro-Arg-Glu-Pro-Gln-Val-Tyr-Thr-Leu-Pro-Pro-Ser-Arg-Glu-Glu</u> | 9.7 |

[1]Polypeptide denominations. Polypeptides I-51(i) and 23 have the same sequence, but were prepared at different times, and correspond to the 23-residue polypeptide of U.S. Pat. No. 4,415,493.
[2]Sequences are shown from left to right and from amino-terminus to carboxy-terminus. Underlined sequences exhibited substantial polyclonal secretion activity.
[3]Ig Found = the amount of polyclonal Ig molecular found in the assay in ug/ml.

As can be seen from an examination of the data of Table 1 and of Table 3, column 4, the polypeptides that were capable of inducing a polyclonal Ig molecule response (underlined polypeptides) all included the tetramer sequence Leu-Pro-Pro-Ser. In addition, polypeptides that contained a sequence of three residues (Arg-Glu-Glu) at the carboxy-terminus of the tetramer also induced a polyclonal response, as did polypeptides that contained a sequence of up to four additional residues (Gln-Val-Tyr-Thr) at the amino-terminus of the tetramer.

Interestingly, polypeptides that contained a Pro residue at the amino-terminus of the 11-residue polypeptide denominated I-51(c) in Table 1; i.e., polypeptides I-51(d-h) induced substantially no polyclonal activity as compared to the polypeptides that contained a Leu-Pro-Pro-Ser sequence but did not include a Pro residue; i.e., polypeptides denominated I-51(a-c). Still more interestingly, substantially complete polyclonal Ig molecule secretion activity was again obtained with the 23-residue sequence provided by polypeptide I-51(i), which corresponds to a polypeptide of U.S. Pat. No. 4,415,493 and polypeptide p23.

Thus, it appears that a requirement for polyclonal Ig molecule response is a polypeptide sequence Leu-Pro-Pro-Ser for a polypeptide of this invention that contains 4 to about 11 amino acid residues, while the full sequence or a sequence with the two carboxy-terminal Glu residues absent [polypeptide I-52(g)] are required to provide similar activation in the longer polypeptide sequences.

2. ELISA Assay

An enzyme-linked immunosorbant assay (ELISA) is a well known solid phase technique. The ELISA utilized to measure polyclonal activation was a so-called "sandwich" assay in which the assayed entity, mouse Ig molecules, are bound to solid phase-bound anti-mouse Ig antibodies and then bound by indicator (alkaline phosphatase)-linked anti-mouse Ig antibodies. The procedures for this assay are discussed below in steps (A), (B) and (C).

(A) Microtiter plate wells (Immulon-2; Dynatech Laboratories, Alexandria, VA) were coated with 100 microliters (ul) of an affinity-purified goat anti-mouse IgM+G+A (H +L) (Zymed, San Francisco, CA) that had HGG-specific antibodies removed by solid phase adsorption, at 2 mg/ml in 0.05 M Tris, pH 9.5. for 4 hours at 37° C. followed by repeated washings with 0.01 M phosphate-buffered 0.15 M NaCl at pH 7.2 (PBS), plus 0.05 percent Tween 20 (polysorbate 20) (PBS-Tween).

(B) 100 Microliters of various dilutions of either the Ig standard or culture supernatants were then admixed in PBS-Tween. The admixture was maintained for a period of 2 hours at 37° C., and was followed by washing with PBS-Tween.

A mixture containing a 1:1:1 weight ratio of an IgM myeloma protein (TEPC 183; Litton Bionetics, Charleston, SC), purified mouse gamma-globulin (Jackson Immunoresearch, Avondale, PA), and an IgA myeloma protein (TEPC 15; Litton Bionetics) was used as the Ig standard.

(C) 100 Microliters of a 1:1000 dilution of alkaline phosphatase-conjugated (AP−) affinity-purified goat anti-mouse IgM+G+A (H +L) (Zymed) in PBS-Tween were then added to the wells. The plates were maintained for a further time period of 2 hours at 37° C., and were thereafter repeatedly washed with PBS-Tween.

Each well then received 100 ul of 1 mg p-nitrophenyl phosphate (Sigma Chemical Co., St. Louis, MO) in 0.05 M carbonate, pH 9.8. The reaction was stopped with 50 ml of 0.3 N NaOH, and the light absorbance at 410 nanometers (nm) was measured by using a Dynatech model MR600 ELISA reader. An interfaced IBM PC running the ELISA-CALC program (Comple-Software, Iowa City, IA) was used to calculate supernatant Ig concentrations based on plots of standard Ig concentration vs $OD_{410}$.

3. BCDF Secretion and Assay

B cell differentiation factor (BCDF) is produced by T cells and acts to induce B cells to differentiate into immunoglobulin (Ig)-secreting cells. The discussion below illustrates that contacting a T cell-containing mixture of lymphocytes with a composition of this invention activates T cells to secrete BCDF into the cell culture supernatant medium. The assay described below measures the activity of polypeptide-containing compositions to stimulate the release of B cell differentiation factor from mouse spleen cells in culture.

In this assay crude spleen cell preparations containing both T and B cells were contacted with polypeptide-containing compositions, and the resulting supernatant containing BCDF was used to induce a B cell enriched, T cell-depleted cell population to differentiate into an Ig secreting population. The secretion of Ig is thus a measure of B cell differentiation induced by BCDF.

Culture supernatants as obtained from the previously described polyclonal antibody response assay were harvested after 24 hours (instead of at day 5) for the BCDF assay. These supernatants contain polypeptide-induced BCDF, which is measured on T cell-depleted spleen culture prepared as follows.

Mouse spleen cells were depleted of T cells by treatment with an anti-T cell antibody cocktail and complement. $50 \times 10^6$ Cells/ml were maintained (incubated) at 4° C. for 30 minutes with a mixture of monoclonal anti-mouse Lyt-1.2 and Thy-1.2 antibodies (New England Nuclear, Boston, MA) that had been pretitrated for optimal cytotoxicity. The cells were washed with phosphate-buffered saline (PBS) containing 5 percent FCS, 1 percent sodium azide and 25 percent complement in which they were incubated 30 minutes at 37° C. The complement was a 4:1 mixture of guinea pig (Pelfreeze) and rabbit-Lowtox mouse (Cedarlane) complements that was pre-adsorbed on ice for 30 minutes against whole mouse blood cells in a volume ratio of 1:10, cells to complement, and stored −70° C. in aliquots. After complement-mediated killing of T cells, viable cells were separated by diluting 5:1 with Hanks balanced salt solution, layering over an equal volume of Ficoll-Hypaque (60:25) mix, centrifuging for a time period of 15 minutes at 2800 rpm and room temperature. Ficoll-Hypaque mix was prepared fresh from 14 percent Ficoll 400 (Pharmacia Fine Chemicals, Piscataway, NJ) and 32.8 percent Hypaque (Winthrop Labs), each in 0.1 percent sodium azide and pyrogen-free water. Viable cells were collected from the interface of the Ficoll-Hypaque gradient, diluted 10:1 in Hanks balanced salt solution, pelleted for 8 minutes at 1800 rpm and room temperature, and were resuspended in complete medium as for whole spleen cells (described above for use in the polyclonal antibody response assay) at $6 \times 10^5$ cells/ml.

For the assay of BCDF activity, these T cell-depleted spleen cell preparations were plated at $3 \times 10^5$ cells/well in microtiter plates (3-42 Microtest II, Falcon Plastics, Oxnard, CA) in 0.3 ml volume of RPM1 1640 medium additionally containing 2 mM L-glutamine, 100 U/ml penicillin, 100 mg/ml streptomycin, $5 \times 10^{-5}$ M 2-mercaptoethanol, 7.5 percent FCS, and p23 peptide at an optimal stimulation concentration of 0.75 ug/ml (0.25 ug/well; about $3 \times 10^{-7}$ M). To these cells were added 20 ul of the supernatants to be assayed for BCDF content. These cell cultures were prepared in duplicate, and were subsequently assayed for Ig secretion after 5 days as for the polyclonal assay.

Results of the BCDF assay are shown in FIG. 1 and Table 3, column 3 ("BCDF Release").

Examination of the graph of FIG. 1 and the data of Table 3, column 3, illustrates that contacting the lymphocytes with compositions of this invention produced BCDF secretion and therefore activation of the T cells. Thus, those data show that compositions containing the polypeptides corresponding in sequence to the carboxy-terminal 7-, 9- and 11-residues [polypeptides I-51(a-c)]and the amino-terminal 21-residues of the 23-residue polypeptide of U.S. Pat. No. 4,415,493, as well as the 23-residue polypeptide itself were capable of inducing BCDF secretion.

4. Proliferation of B Cells and Assay

Induction of B cell multiplication or proliferation is another aspect of the lymphocyte activating properties of the polypeptides of this invention when used as the active ingredient in a composition of this invention to contact B cells. Such cellular proliferation is conveniently assayed by measuring the uptake of a radiolabeled nucleic acid that is required for the production of new cells. The assay described below measures the ability of a studied polypeptide-containing composition to induce the proliferation of a cultured murine spleen cell population in the presence of interleukin-1 (IL-1).

Here, spleen cells depleted of T-cells as described in BCDF assay were further depleted of macrophages by double passage of $50 \times 10^6$ cells through 9 ml columns of Sephadex G-10 (Pharmacia) that had been equilibrated in Hanks' balanced salts solution (BSS) containing 5 percent FCS at 37° C. Cells were eluted with 6 ml of warm BSS containing 5 percent FCS.

Triplicate cultures of $3 \times 10^5$ cells/0.2 ml were plated in microtiter plates (3040 MicroTest II, Falcon Products, Oxnard, CA) in RPMI 1640 medium (Flow Laboratories, Inc., Rockville, MD), supplemented with 2 mM L-glutamine, 100 U/ml penicillin, 100 ug/ml streptomycin (Microbiological Associates, Bethesda, MD), $5 \times 10^{-5}$ M 2-mercaptoethanol, and 1x concentration of BME vitamins (GIBCO), and were maintained (incubated) at 37° C. in air containing 5 percent $CO_2$.

Polypeptides for study were admixed at day 0 at the same concentrations as for the polyclonal antibody response assay. Initially, the following mitogenic materials were used as control substances: Lipopolysaccharide (LPS) (055; B5, Difco); purified human IL-1 (Cistron) titrated for optimal synergystic effect; concanavalin a (Con A; Miles Laboratories, Elkhart, IN); purified Fc fragment prepared from Human myeloma $IgG_1$ by the papain cleavage procedure of Porter, *Biochem. J.*, 73, 119–126 (1957), and synthetic polypeptide p23 (described hereinabove). Subsequently, polypeptide studies were performed using IL-1 constitutively at a 1:150 dilution determined optimal for its effect.

After 2 days of maintenance with a polypetide-containing composition, the cultures were pulsed with 1 uCi of tritiated thymidine [$^3$H]TdR (New England Nuclear, Boston, MA, NET-027) per 0.05 ml, and were harvested 24 hours later with an automatic cell harvester (model M24V, Brandel, Rockville, MD). The resulting cell-containing strips were dried, placed in 5 ml scintillation flour (Betamax; Beckman), and counted in a scintillation counter. Results are expressed as mean counts per minute (cpm) of triplicate cultures ± standard deviation for Table 2, below, and expressed as a stimulation index (SI) for FIG. 2; where SI equals the ratio of the counts per minute (cpm) incorporated to the cpm of background, and where background cpm is counts incorporated with IL-1 but in the absence of polypeptide or mitogen.

TABLE 2

| SYNERGY BETWEEN p23 AND IL-1 IN PROLIFERATION OF MURINE B CELLS[1] | | | | |
|---|---|---|---|---|
| p23[2] | IL-1[3] | mitogen[4] | cpm[5] | SD[6] |
| 0 | 0 | 0 | 552 | ±215 |
| 0 | 1:150 | 0 | 2639 | ±956 |
| 1.5 | 0 | 0 | 294 | ±213 |
| 1.5 | 1:150 | 0 | 17,073 | ±1390 |
| 0 | 0 | LPS (30) | 40,257 | ±31,978 |
| 0 | 0 | Con A (2) | 1,829 | ±465 |
| 0 | 0 | Fc (75) | 671 | ±306 |

[1]B cells utilized were depleted of T cells and macrophages.
[2]Concentration of polypeptide p23 in ug/ml.
[3]IL-1 was absent (0) or present at a dilution of 1:150 of that found optimal for its effect.
[4]Concentration of exogenously supplied mitogen in ug/ml; LPS = lipopolysaccharide; Con A = concanavalin A; and Fc = purified Fc fragment portion from human myeloma IgG1 protein.
[5]cpm = counts per minute.
[6]SD = standard deviation.

5. Further BCDF-Related Results

The previously discussed results have illustrated that contacting T cells with a composition of this invention induces BCDF secretion and that a BCDF-containing supernatant could thereafter be utilized to differentiate B cells in the presence and absence of T cells and induce Ig molecule secretion. Those results also illustrated that all of the polypeptides studied; i.e., those having the carboxy-terminal 7,9,11,13,15,17,19,21 and 23 residue sequences of the 23-residue polypeptide of U.S. Pat. No. 4,415,493 induced B cells to proliferate. As a further control study, it was also of interest to determine whether exogenously supplied BCDF and a proliferation-inducing polypeptide would be sufficient to cause a T cell-depleted B cell culture to secrete polyclonal antibodies.

Thus, a T cell-depleted, B cell-containing lymphocyte culture was prepared as described previously for the BCDF assay. To a series of such cell cultures were added equimolar amounts of polypeptides containing the above 7,9,11,13,15,17, 19,21 and 23 residue sequences as described for the proliferation study, and 10 microliters each of supernatant from spleen cells stimulated with polypeptide p23, as was done in the first part of the BCDF assay. The cell preparations were then cultured as described for the polyclonal antibody response assay, and the presence of antibody was determined.

The results of this assay are shown in the right-handmost column (column 5) of Table 3, below, and illustrate that the presence of individually effective amounts of BCDF and any of the polypeptides assayed is sufficient to induce polyclonal antibody secretion. Table 3 also contains a summation of the previously discussed results for the carboxy-terminal polypeptide sequences assayed; i.e., B cell proliferation —column 2; T cell BCDF release —column 3; and polyclonal antibody secretion from mixed spleen cells —column 4.

TABLE 3

BIOLOGICAL PROPERTIES OF Fc-DERIVED SYNTHETIC CARBOXY TERMINUS PEPTIDES

| Polypeptide[1] | | | | Ig Secretion[4] | |
| --- | --- | --- | --- | --- | --- |
| I-51 | C-term. residues | Prolif.[2] | BCDF Release[3] | peptide alone | peptide + BCDF |
| (a) | 7 | + | + | + | + |
| (b) | 9 | + | + | + | + |
| (c) | 11 | + | + | + | + |
| (d) | 13 | + | − | − | + |
| (e) | 15 | + | − | − | + |
| (f) | 17 | + | − | − | + |
| (g) | 19 | + | − | − | + |
| (h) | 21 | + | − | − | + |
| (i) | 23 | + | + | + | + |

[1]Polypeptides utilized in studies named I-51(a-i) as per Table 1, and by the number of carboxy-terminal (C-term.) residues of the 23-residue polypeptide sequence of U.S. Pat. No. 4,415,493.
[2]B cell proliferation in the presence of each polypeptide and IL-1.
[3]BCDF release by T cells.
[4]Polyclonal Ig molecule secretion from a spleen cell mixture using compositions containing the individual polypeptides (peptide alone), and from a T cell-depleted B cell culture using compositions containing individual polypeptides and BCDF (peptide + BCDF).

6. Activity Differences

The data discussed before illustrates that the polypeptides of this invention have lymphocyte-activating activities that are similar to those of the 23-residue polypeptide of U.S. Pat. No. 4,415,493. Those results also illustrate that the lymphocyte-activities of the polypeptides of this invention and of that 23-residue polypeptide are different in their abilities to induce BCDF release and polyclonal Ig molecule secretion from the longer polypeptides that include the sequences of a polypeptide of this invention and also include the Pro residue that corresponds to position 346 of the human IgG1 myeloma protein, as well as up to nine residues to the amino-terminus of that Pro residue.

Further differences in activity have also been found in studies that are presently underway. Initial data from these studies indicate that the Fc fragment portion of the IgG1 human myeloma protein, polypeptide p23, and polypepties I-51(i) and I-52(g), whose sequences are shown in Table 1, are all capable of inducing the secretion of a prostaglandin E from each of three cell line cultures into the culture medium, while the polypeptides of this invention such as the polypeptides denominated I-51(a), I-51(b) and I-51(c) of Table 1 are incapable of inducing the secretion of a prostaglandin E from similar cells.

The cell lines used in these studies were: (1) murine plastic-adherent macrophages; (2) human plastic-adherent monocytes; and (3) the murine macrophage-like cell line denominated P388.D$_1$ [Snyderman et al., *J. Immunol.*, 119, 2060 (1977)]. Here, a composition containing 25 ug/ml of polypeptide p23 or an equimolar amount of another studied polypeptide was contacted with the cells for a period of 24 hours. Thereafter, the cell culture supernatant was assayed for the presence of a prostaglandin E using a commercially available radioimmune assay (Seragen).

The foregoing is intended as illustrative of the present invention but not limiting. Numerous variations and modifications may be effected without departing from true spirit and scope of the invention.

What is claimed is:

1. A polypeptide containing 4 to about 11 residues, and having an amino acid residue sequence, written from left to right and in the direction from amino-terminus to carboxy-terminus, that corresponds to the formula:

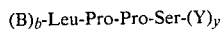

(B)$_b$-Leu-Pro-Pro-Ser-(Y)$_y$ and the pharmaceutically acceptable non-toxic salts thereof, wherein B is the amino acid residue Thr or is a polypeptide, written from left or right and in the direction from amino-terminus to carboxy-terminus, selected from the group consisting of Tyr-Thr, Val-Tyr-Thr and Gln-Val-Tyr-Thr;

Y is the amino acid residue Arg, or is a peptide, written from left to right and in the direction from amino-terminus to carboxy-terminus, selected from the group consisting of Arg-Glu and Arg-Glu-Glu; and b and y are each independently one or zero, such that when either or both of b and y are zero, the respective B and Y are absent, and when either or both of b and y are one, the respective B and Y are present.

2. The polypeptide according to claim 1 wherein b and y are both zero.

3. The polypeptide according to claim 1 wherein b is zero, y is one and y is Arg-Glu-Glu.

4. The polypeptide according to claim 1 wherein b and y are both 1, B is Tyr-Thr and Y is Arg-Glu-Glu.

5. The polypeptide according to claim 1 wherein b and y are both 1, B is Gln-Val-Tyr-Thr and Y is Arg-Glu-Glu.

6. A lymphocyte activating composition comprising a diluent amount of a physiologically tolerable carrier admixed with an effective amount of a polypeptide active ingredient, said polypeptide containing 4 to about 11 residues, and having an amino acid residue sequence, written from left to right and in the direction from amino-terminus to carboxy-terminus, that corresponds to the formula:

(B)$_b$-Leu-Pro-Pro-Ser-(Y)$_y$ and the pharmaceutically acceptable non-toxic salts thereof, wherein B is the amino acid residue Thr or is a polypeptide, written from left or right and in the direction from amino-terminus to carboxyterminus, selected from the group consisting of Tyr-Thr, Val-Tyr-Thr and Gln-Val-Tyr-Thr;

Y is the amino acid residue Arg, or is a peptide, written from left to right and in the direction from amino-terminus to carboxy-terminus, selected from the group consisting of Arg-Glu and Arg-Glu-Glu; and b and y are each independently one or zero, such that when either or both of b and y are zero, the respective B and Y are absent, and when either or both of b and y are one, the respective B and Y are present.

7. The composition according to claim 6 wherein said polypeptide is present at a concentration of about $1 \times 10^{-7}$ to about $1 \times 10^{-3}$ molar, and said carrier is an aqueous liquid.

8. A method of activating lymphocytes comprising contacting lymphocytes with a unit dose of composition containing a diluent amount of a physiologically tolerable carrier admixed with an effective amount of a polypeptide active ingredient, said polypeptide containing 4 to about 11 residues, and having an amino acid residue sequence, written from left to right and in the direction from amino-terminus to carboxy-terminus, that corresponds to the formula:

(B)$_b$-Leu-Pro-Pro-Ser-(Y)$_y$ and the pharmaceutically acceptable non-toxic salts thereof, wherein B is the amino acid residue Thr or is a polypeptide, written from left or right and in the direction from amino-terminus to carboxyterminus, selected from the group consisting of Tyr-Thr, Val-Tyr-Thr and Gln-Val-Tyr-Thr;

Y is the amino acid residue Arg, or is a peptide, written from left to right and in the direction from amino-terminus to carboxy-terminus, selected from the group consisting of Arg-Glu and Arg-Glu-Glu; and b and y are each independently one or zero, such that when either or both of b and y are zero, the respective B and Y are absent, and when either or both of b and y are one, the respective B and Y are present.

9. The method according to claim 8 wherein said contacting is carried out in vivo in a mammal.

10. The method according to claim 9 wherein said unit dose contains about 200 micrograms to about 20 milligrams of said polypeptide per kilogram of body weight of said mammal.

11. The method according to claim 10 wherein said unit dose is contacted with said lymphocytes daily.

12. The method according to claim 8 wherein said contacting is carried out in vitro in a cell culture.

13. The method according to claim 12 wherein said unit dose contains about $1 \times 10^{-7}$ to about $\times 10^{-3}$ molar polypeptide per $1 \times 10^6$ cells per milliliter of cell culture.

14. The method according to claim 8 wherein said contacted lymphocytes are T cells.

15. The method according to claim 8 wherein said contacted lymphocytes are B cells.

* * * * *

UNITED STATES PATENT AND TRADEMARK OFFICE
CERTIFICATE OF CORRECTION

PATENT NO. : 4,683,221
DATED : July 28, 1987
INVENTOR(S) : William O. Weigle et al.

It is certified that error appears in the above-indentified patent and that said Letters Patent is hereby corrected as shown below:

Column 1, line 3 after the heading "Description" and before the heading "Technical Field", insert the following paragraph:

--This invention was made with government support under Contract No. AI 15761 awarded by the National Institutes of Health. The government has certain rights in the invention.--

Signed and Sealed this

Fourth Day of January, 1994

Attest:

BRUCE LEHMAN

*Attesting Officer*  *Commissioner of Patents and Trademarks*